United States Patent
Ballard et al.

(10) Patent No.: US 6,235,301 B1
(45) Date of Patent: May 22, 2001

(54) TERMITE BAIT

(75) Inventors: James Bruce Ballard, Medford, NJ (US); Sherman H. Trimm, Langhorne, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/472,396

(22) Filed: Dec. 27, 1999

Related U.S. Application Data

(63) Continuation of application No. 08/916,476, filed on Aug. 22, 1997, now Pat. No. 6,071,529, which is a continuation of application No. 08/614,422, filed on Mar. 12, 1996, now Pat. No. 5,695,776.

(51) Int. Cl.[7] .......................... A01N 25/00; A01N 25/08; A01N 25/34
(52) U.S. Cl. ........................... 424/405; 424/408; 424/409
(58) Field of Search .................... 424/405, 408, 424/409

(56) References Cited

U.S. PATENT DOCUMENTS

| | | | |
|---|---|---|---|
| 5,329,726 | * 7/1994 | Thorne et al. | 43/124 |
| 5,695,776 | * 12/1997 | Ballard et al. | 424/408 |
| 5,950,356 | 9/1999 | Nimocks | 43/131 |
| 6,003,266 | 12/1999 | Woodruff | 43/124 |

FOREIGN PATENT DOCUMENTS

WO 93/23998    12/1993    (WO) .

OTHER PUBLICATIONS

Perimeter Patrol System, PPS–30T Termite Starter Kit Advertisement, B & G Equipment Company, Jul. 22, 1998.

* cited by examiner

Primary Examiner—Shelley A. Dodson
(74) Attorney, Agent, or Firm—FMC Corporation

(57) ABSTRACT

The invention provides a method and apparatus for controlling termites. The invention provides a more attractive and durable termite bait by providing a thin flat block of wood with grooves and impregnating the surface of the wood with a slow acting toxicant.

10 Claims, 3 Drawing Sheets

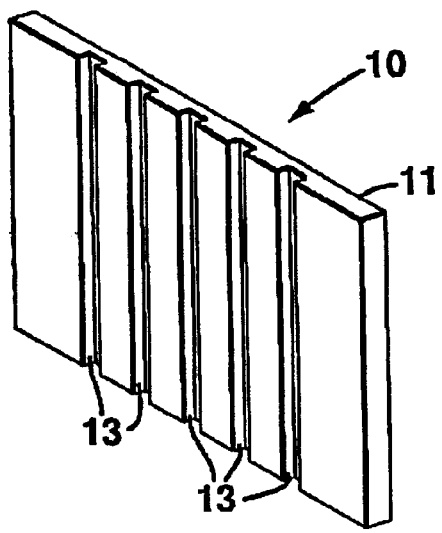
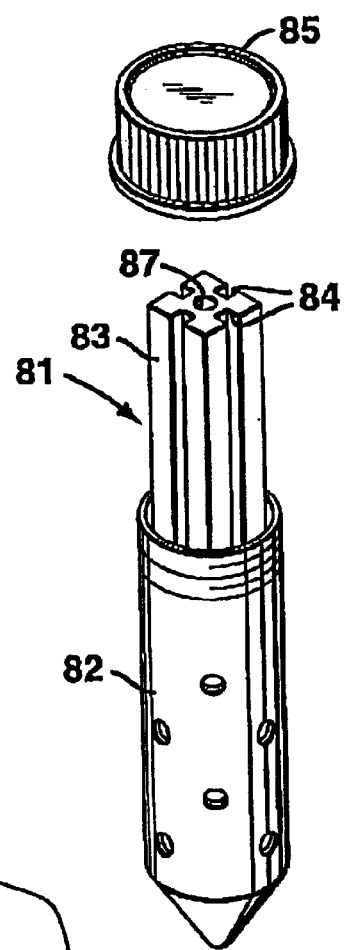
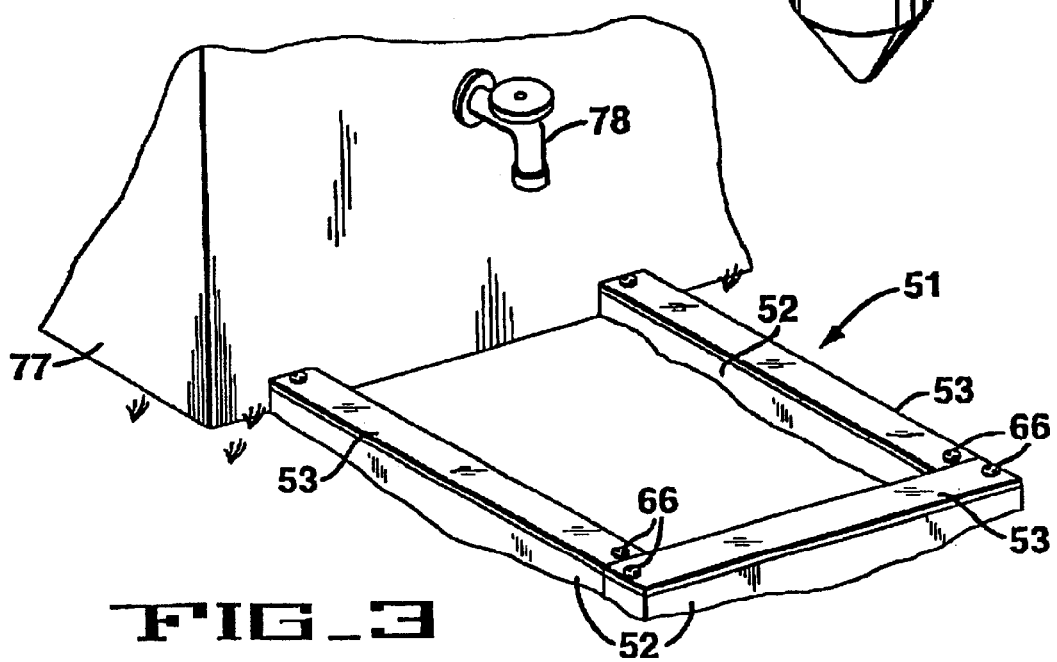

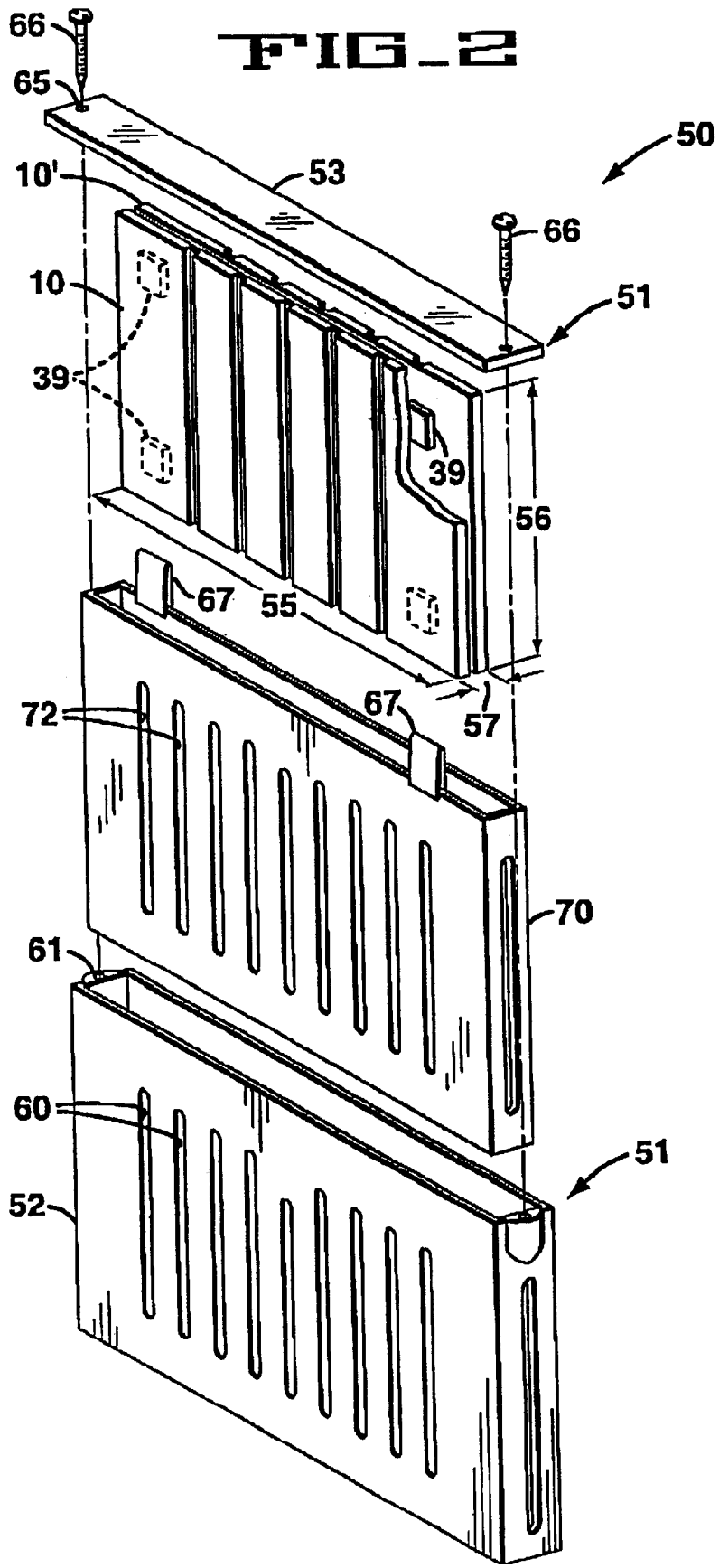

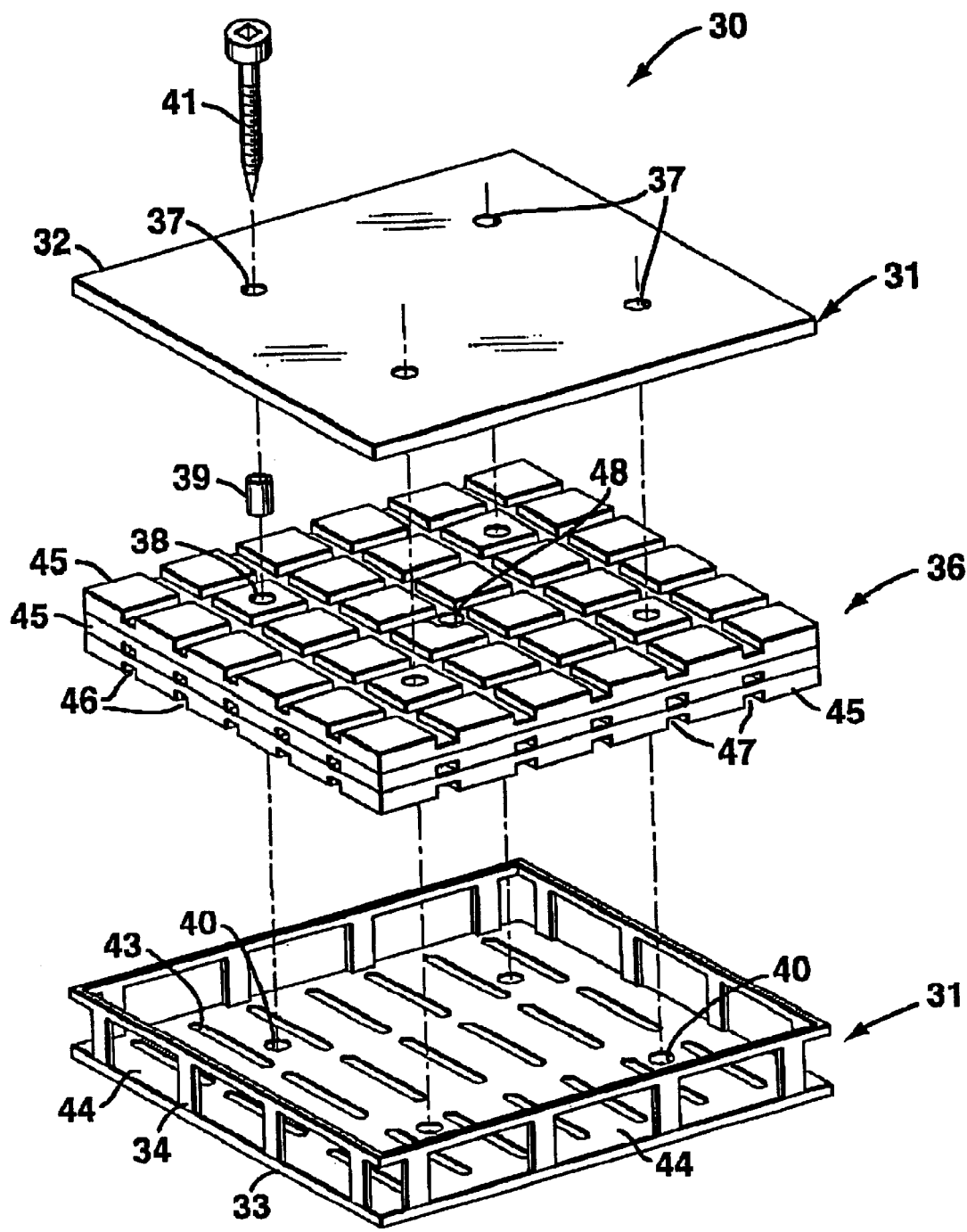
FIG_4

TERMITE BAIT

This application is a continuation application of Ser. No. 08/916,476, filed on Aug. 22, 1997, now U.S. Pat. No. 6,071,529, which is a continuation application of Ser. No. 08/614,422, filed on Mar. 12, 1996, which issued as U.S. Pat. No. 5,695,776 on Dec. 9, 1997.

BACKGROUND OF THE INVENTION

The present invention relates generally to the control of termites and other social insects. In particular, the present invention relates to the control of such insects using an apparatus containing bait impregnated with a slow acting toxicant. For a discussion of social insects, see generally U.S. Pat. No. 5,152,992. That patent is incorporated by reference herein to the extend it discusses social insects and their habits.

In the prior art, various techniques of spraying fast acting insecticides in a structure are used to eliminate social insects such as termites in the structure. For eliminating social insects in the ground instruments with cardboard or sawdust bait were used.

SUMMARY OF THE INVENTION

It is an object of the invention to provide an apparatus and method for eliminating social insects such as termites in a structure.

It is another object of the invention to provide an apparatus and method for eliminating social insects in the ground.

The invention provides a method and apparatus for providing a more attractive and durable termite bait, which comprises a thin flat block of wood with grooves.

BRIEF DESCRIPTION OF THE DRAWINGS

FIG. 1 is a perspective view of a preferred embodiment of the inventive termite bait.

FIG. 2 is an exploded view of a bait station, which utilizes the inventive termite bait.

FIG. 3 is a schematic view of the use of the embodiment illustrated in FIG. 2.

FIG. 4 is an exploded view of another preferred embodiment of a bait station.

FIG. 5 is another embodiment of the invention for use in a tubular station.

DESCRIPTION OF THE PREFERRED EMBODIMENTS

FIG. 1 is a perspective view of a preferred embodiment of the inventive termite bait 10, formed by a block of wood 11, which is thin, flat and rectangular. Some possible woods which may form the termite bait are spruce, pine and fir. A plurality of parallel grooves 13 are cut along one or more sides of the block of wood 11. The length of the groove extends from one end of the block of wood to the other end of the block of wood, as shown. It is preferable that the width of the groove is ⅛ inch, which is approximately 3.175 mm. The depth of the grooves go at least half way through the block of wood 11. The grooves may be as wide as one inch in width (25.4 mm) or as narrow as ¹⁄₃₂ inch (0.794 mm) in width. In this embodiment the grooves 13 are on one side of the block of wood 11. The grooves 13 may be on all six sides of the rectangular block of wood 11.

The surface of the block of wood 11 is treated with a slow acting toxicant. The amount of toxicant needed to control termites will vary, depending on the particular toxicant used, but in general an amount between about 1 and about 5,000 parts per million (ppm) of toxicant to bait may be utilized. For example, if sulfluramid is the toxicant, an amount between about 10 and about 200 ppm may be used, preferably between about 50 and about 100 ppm, and if abamectin is the toxicant, an amount between about 10 and about 200 ppm may be used, preferably between about 50 and about 100 ppm.

In FIG. 2 an outdoor station 50 has an outer box 51, comprising the body 52, and a top cover 53. The body 52 has a plurality of apertures 60 which extend along the side of the body 52. The body 52 has a plurality of screw holes 61. The top cover 53, which extends along the length and thickness of the outer box 51 has a plurality of screw holes 65, which mate with the screw holes 61 of the body 52. A plurality of screws 66 are provided to pass through the screw holes 65 of the top cover 53 and screw into the screw holes 61 of the body 52.

A bait holder 70 also has a box shape, and is small enough to fit into the outer box 51. The bait holder 70 has a plurality of apertures 72. The inventive bait 10 is placed in the bait holder 70. The bait 10 has a length 55, width 56, and thickness 57, wherein the length 55 is at least six times the thickness 57, and wherein the width 56 is at least five times the thickness 57. The bait 10 is attached to an identical bate 10' by blocks of double sided adhesive spacers 39. The bait holder 70 has a plurality of foldable tabs 67 to allow easier removal of the bait holder 70 from the body 52. Other means may be provided to facilitate the removal of the bait holder 70 from the body 52.

FIG. 3 is a schematic illustration of a plurality of the outdoor stations in operation. Adjacent to a structure 77, there may be areas that have a higher chance of attracting termites, such as near a water source such as a faucet 78. A U-shaped trench is made around the area of the faucet 78 and three bodies 52 of outer boxes 51 are placed in the trenches. A bait holder 70 (FIG. 2) is then placed in each body 52 of an outer box 51. A top cover 53 is then secured to each body 52 by the screws 66. On a periodic basis, possibly every six months, the screws 66 are removed, the bait holder 70 is also removed and inspected. If the inventive bait 10 is intact, the bait holder 70 is put back in the body 52 and the top cover 53 is resecured. If the inventive bait 10 needs replacing, a new bait holder 70 with new bait 10 is placed in the body 52. The periodic inspection allows the monitoring for termites.

The slow acting toxicant in the bait 10 allows for the control of an entire colony. The high surface area to volume ratio of the bait 10, due to the ratio between the length 55, width 56, and thickness 57 allows for a large surface area which protects against termites and provides a large surface area for the slow acting toxicant. The grooves 13 increase the attractiveness of the bait 10 to termites and the attractive surface area. This is because it is easier for termites to tube over such grooves 13. The use of wood is also preferable to the prior art cardboard in that wood is more durable and thus lasts longer.

In another method of operation, the outer box 51 may be laid flat on the ground and covered with mulch.

FIG. 4 illustrates another embodiment of a termite station 30 using another embodiment of the termite bait 36. The bait station 30 has an outer cover 31, comprising a tinted transparent plastic top cover 32, an opaque plastic bottom cover 33, and an opaque side cage 34 between the top cover 32 and bottom cover 33 and around the outer edges of the top cover 32 and the bottom cover 33. The outer cover 31, forms a flat box shape, with the top cover 32 forming a side of the flat box with the greatest area, and the bottom cover 33 forming the other side of the flat box with the greatest area, and the side cage 34 forming the four sides of the flat box with the smallest areas. Between the top cover 32 and the bottom cover 33 and within the perimeter formed by the side cage 34 is the inventive bait 36 impregnated with a slow acting toxicant such as sulfluramid. The side cage 34 is welded to the bottom cover 33.

The top cover 32 has a plurality of top cover screw holes 37. The bait 36 has a plurality of screw holes 38, which mate with the top cover screw holes 37. A plurality of spacers 39 are provided, with a spacer 39 in each bait screw hole 38. The bottom cover 33 has a plurality of bottom cover screw holes 40, which mate with the bait screw holes 38. A plurality of screws 41 are provided with a screw 41 passing through a top cover screw hole 37 and its mating bait screw hole 38, and its mating bottom cover screw hole 40. As the screw 41 passes through the bait screw hole 38 it also passes through a spacer 39. The screws 41 provide a means for mounting the bait station 30 to a wall of a structure. The screws 41 also secure the top cover 32 to the bottom cover 33 so that the edges of the top cover 32 press against the side cage 34 forming the outer cover 31 and making the outer cover 31 tamper resistant. The heads of the screws 41 are square socket heads.

The bottom cover 33 has a plurality of bottom cover apertures 43 in the shape of slots. Side apertures 44 are formed at the junction where the side cage 34 and the bottom cover 33 meet. The bottom cover apertures 43 and the side apertures 44 are small enough to prevent children from touching the bait 36, thus helping to make the bait station 30 tamper resistant.

The bait 36 comprises three sheets of wood 45. Each sheet of wood 45 has a first set of parallel grooves 46 and a second set of parallel grooves 47 which are perpendicular to the first set of parallel grooves 46. The first and second set of parallel grooves 46, 47 are formed on one or more sides of each sheet 45. The first and second set of parallel grooves have a width of approximately 1/8 inch. A central aperture 48 allows termites to pass to different layers of the sheets 45.

The operation of this bait station 30 is the similar to the bait station 50 above, but is adapted to be mounted on the walls of a structure. The tinted transparent plastic top cover 32 allows inspection of the bait 36 without removing the bait station 30.

By using a plurality of thin sheets of wood 45 for the bait 36, the surface area to volume ratio is increased, making the bait 36 more attractive to termites and providing a higher ratio of slow acting toxicant to volume of bait 36. Providing a first set and second set of grooves 46, 47 in different directions, also increases the attractiveness of the bait 36 to termites, when it is unknown as to which direction the termites will be approaching the bait 36.

FIG. 5 illustrates a bait 81 for use in a linear bait station 82. The linear station 82 used in this example is cylindrical. For this reason the bait 81 is a rectangular block of wood 83, with grooves 84 on the sides of the block of wood 83 extending along the length of the block of wood 83. A cap 85 is used to hold the bait 81 in the linear station 82. An aperture 87 is drilled in the center of the block of wood 83 to remove some of the bulk of the wood.

Other embodiments of the inventive bait may be used in other termite traps. In other embodiments the block of wood may be formed using other types of wood to attract different types of termites. Pine would be used for one type of termite and oak may be used for another type of termite. Wood particles may be pressed together to form a solid block, which would be the block of wood. Another embodiment when providing grooves ones opposite sides of a block of wood, could stagger the grooves from one side to the other.

While preferred embodiments of the present invention have been shown and described herein, it will be appreciated that various changes and modifications may be made therein without departing from the spirit of the invention as defined by the scope of the appended claims.

What is claimed is:

1. An apparatus for controlling termites comprising a block, wherein at least one groove extends across a surface of the block; wherein a slow acting toxicant impregnates the surface of the block; and wherein the at least one groove extending across the surface of the block increases the attractiveness of the apparatus.

2. The apparatus of claim 1, wherein said slow acting toxicant is selected from the group consisting of boric acid, borate, hydramethylnon, macrolide antibiotics, insect growth regulators, biological agents, protozoacides, termiticides, and slow acting poisons.

3. The apparatus of claim 1, wherein the slow acting toxicant is selected from the group consisting of sulfluramid abamectin, hydramethylnon, hexaflumuron, spinosyn A, spinosyn D and mixtures thereof.

4. An apparatus for controlling termites comprising a block, wherein at least one groove extends across a surface of the block and wherein the at least one groove extending across the surface of the block increases the attractiveness of the apparatus.

5. The apparatus of claim 4, wherein said block is contained in an outer structure.

6. The apparatus of claim 5, wherein the outer structure is a tubular station.

7. The apparatus of claim 5, wherein said block contains a plurality of grooves.

8. An apparatus for controlling termites comprising a termite bait, wherein at least on groove extends across a surface of the termite bait and wherein the at least one groove extending across the surface of the termite bait increases the attractiveness of the apparatus.

9. The apparatus of claim 8, wherein said termite bait is contained in an outer structure.

10. The apparatus of claim 9, wherein said termite bait contains a plurality of grooves.

* * * * *